United States Patent [19]

Huff et al.

[11] Patent Number: 5,338,851

[45] Date of Patent: Aug. 16, 1994

[54] SYNTHESIS OF CIS-DECAHYDROISOQUINOLINE-3-CARBOXYLIC ACIDS

[75] Inventors: Bret E. Huff, Indianapolis; Vien V. Khau, Carmel; Michael J. Martinelli; Barry C. Peterson, both of Indianapolis, all of Ind.

[73] Assignee: Eli Lilly and Company, Indianapolis, Ind.

[21] Appl. No.: 40,759

[22] Filed: Mar. 31, 1993

[51] Int. Cl.$^5$ ............... C07D 217/14; C07D 217/06; C07D 217/04

[52] U.S. Cl. ................. 546/141; 546/145; 546/147; 546/150

[58] Field of Search ........... 546/141, 145, 147, 150

[56] References Cited

U.S. PATENT DOCUMENTS 4,902,695 2/1990 Ornstein .................... 514/307

OTHER PUBLICATIONS

Aster et al., *Tetr. Lett.*, vol. 22 pp. 141–144 (1981).
Ornstein, Arnold, Augenstein, and Paschal, *J. Org. Chem.*, 56, 4388–92 (1991).
Ornstein et al., *J. Med. Chem.*, 35, 3547–60 (1992).
Asher, Becu, Anteunis, and Callens, *Tetr. Lett.*, 22, 141–44 (1981).
Shono, Matsumura, and Tsubata, *J. Am. Chem. Soc.*, 103, 1172–76 (1981).
Utimoto et al., *Tetr. Lett.*, 22, 4279–80 (1981).
Thaning and Wistrand, *Helvetica Chimica Acta*, 69, 1711–17 (1986).
Shono, Hamaguchi, and Matsumura, *J. Am. Chem. Soc.*, 97, 4264–68 (1975).
Shono et al, *J. Am. Chem. Soc.*, 104, 6697–6703 (1982).
Shono, *Tetrahedron*, 40, 811–50 (1984).

*Primary Examiner*—C. Warren Ivy
*Assistant Examiner*—D. Margaret M. Mach
*Attorney, Agent, or Firm*—James P. Leeds

[57] ABSTRACT

This invention provides a process for the synthesis of cis-decahydroisoquinoline-3-carboxylic acids and provides intermediates in the synthesis thereof.

15 Claims, No Drawings

SYNTHESIS OF CIS-DECAHYDROISOQUINOLINE-3-CARBOXYLIC ACIDS

BACKGROUND OF THE INVENTION

The role of excitatory amino acids (EAA), such as glutamic acid and aspattic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. The excitatory amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane or the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic transmission along excitatory pathways, but also participate in the modification of synaptic connections during development. These receptors also affect changes in the efficiency of synaptic transmission throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. Excitatory amino acid excitotoxicity has been implicated in the pathophysiology of a number of neurological disorders. This excitotoxicity has been implicated in the pathophysiology of acute and chronic neurodegenerative conditions including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, perinatal hypoxia, cardiac arrest, hypoglyemic neuronal damage, ocular damage and retinopathy, and idiopathic and drug-induced Parkinson's Disease. Other neurological conditions, that are caused by glutamate dysfunction, may require neuromodulation. These other neurological conditions include muscular spasms, migraine headaches, urinary incontinence, psychosis, opiate tolerance and withdrawal, anxiety, emesis, brain edema, chronic pain, convulsions, and tardive dyskinesia. The use of a neuroprotective agent, such as an EAA receptor antagonist, is believed to be useful in treating these disorders and/or reducing the amount of neurological degeneration associated with these disorders. The medical consequences of such neuronal degeneration makes the abatement of these degenerative neurological processes an important therapeutic goal.

A recent report shows that a series of 6-substituted decahydroisoquinoline-3-carboxylic acids act as competitive NMDA receptor antagonists and are suitable for use as neuroprotective agents in a variety of acute and chronic neurodegenerative disorders. Ornstein et al., *J. Med. Chem.*, 35, 3547-3560 (1992). One compound from this series, (±)-(3SR,4aRS, 6SR, 8aRS)-6-(phosphonomethyl)-decahydroisoquinoline-3-carboxylic acid, is a very potent and selective neuroprotective agent against excessive NMDA receptor activation in vivo when administered systemically in rats and in mice. Schoepp, ornstein, Salhoff, and Leander, *J. Neural Transm.*, 85, 131-143 (1991). This compound effectively blocks NMDA-induced convulsions in neonatal rats. This compound also provides neuroprotection against NMDA receptor-induced lethality in mature mice and rats. Surprisingly, the 3S isomer of this compound is active as an NMDA receptor antagonist, while the 3R isomer is inactive. Ornstein & Klimkowski, *Excitatory Amino Acid Receptors: Design of Agonists and Antagonists*, 183-200 (1992). Therefore, this agent, as well as other compounds in the series, may prove therapeutically useful in treating acute pathological conditions that involve glutamate excitotoxicity.

SUMMARY OF THE INVENTION

The present invention relates to a process for the stereocontrolled synthesis of cis-decahydroisoquinoline-3-carboxylic acids. These compounds are useful in the synthesis of the above mentioned NMDA excitatory amino acid receptor antagonists. More specifically, the present invention relates to processes for preparing a compound of the formula

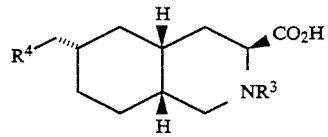

III wherein
$R^3$ is hydrogen, $C_1$-$C_6$ alkyl, arylalkyl, acyl, $C_1$-$C_6$ alkylsulfonyl, arylsulfonyl, alkoxycarbonyl, aryloxycarbonyl, or arylalkoxycarbonyl;
$R^4$ is $CO_2R^5$, $CON(R^5)_2$, $PO(OR^5)_2$,

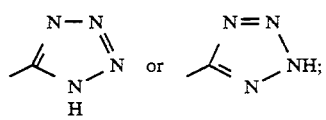

$R^5$ is hydrogen, $C_1$-$C_6$ alkyl, or arylalkyl.

This invention also relates to a process for the stereoselective preparation of 6-substituted decahydroisoquinolines of the formula

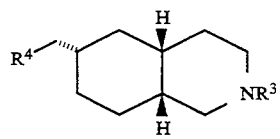

IV wherein $R^3$ is hydrogen, $C_1-C_6$ alkyl, arylalkyl, acyl, $C_1-C_6$ alkylsulfonyl, arylsulfonyl, alkoxycarbonyl, aryloxycarbonyl, or arylalkoxycarbonyl;

$R^4$ is $CO_2R^5$, $CON(R^5)_2$, $PO(OR^5)_2$,

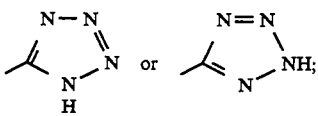

$R^5$ is hydrogen, $C_1-C_6$ alkyl, or arylalkyl.

This invention also relates to compounds useful for the preparation of cis-decahydroisoquinoline-3-carboxylic acids. More specifically, the present invention relates to a compound of the formula

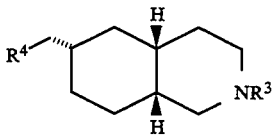 IV wherein
$R^3$ is hydrogen, $C_1-C_6$ alkyl, arylalkyl, acyl, $C_1-C_6$ alkylsulfonyl, arylsulfonyl, alkoxycarbonyl, aryloxycarbonyl, or arylalkoxycarbonyl;

$R^4$ is $CO_2R^5$, $CON(R^5)_2$, $PO(OR^5)_2$,

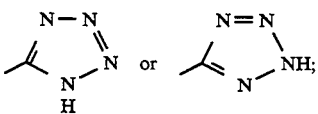

$R^5$ is hydrogen, $C_1-C_6$ alkyl, or arylalkyl.

The present invention also relates to other compounds useful for the preparation of cis-decahydroisoquinoline-3-carboxylic acids. More specifically, the present invention relates to a compound of the formula

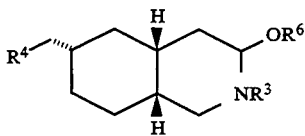 V wherein
$R^3$ is hydrogen, $C_1-C_6$ alkyl, arylalkyl, acyl, $C_1-C_6$ alkylsulfonyl, arylsulfonyl, alkoxycarbonyl, aryloxycarbonyl, or arylalkoxycarbonyl;

$R^4$ is $CO_2R^5$, $CON(R^5)_2$, $PO(OR^5)_2$,

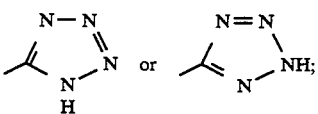

$R^5$ is hydrogen, $C_1-C_6$ alkyl, or arylalkyl; $R^6$ is hydrogen, $C_1-C_4$ alkyl, —OH, —O—($C_1-C_4$ alkyl), or —O—aryl.

The present invention also relates to another group of compounds useful for the preparation of cis-decahydroisoquinoline-3 -carboxylic acids. More specifically, the present invention relates to a compound of the formula

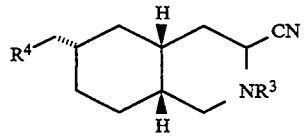 VI wherein
$R^3$ is hydrogen, $C_1-C_6$ alkyl, arylalkyl, acyl, $C_1-C_6$ alkylsulfonyl, arylsulfonyl, alkoxycarbonyl, aryloxycarbonyl, or arylalkoxycarbonyl;

$R^4$ is $CO_2R^5$, $CON(R^5)_2$, $PO(OR^5)_2$, $R^5$ is hydrogen, $C_1-C_6$ alkyl, or arylalkyl.

DETAILED DESCRIPTION OF THE INVENTION

The term "$C_1-C_6$ alkyl" represents a straight or branched alkyl chain having from one to six carbon atoms. Typical $C_1-C_6$ alkyl groups include methyl, ethyl, n-propyl, isopropyl, n-butyl, isobutyl, sec-butyl, t-butyl, n-pentyl, isopentyl, and n-hexyl. The term "$C_1-C_6$ alkyl" includes within it the term "$C_1-C_4$ alkyl". Typical $C_1-C_4$ alkyl groups include methyl, ethyl, n-propyl, isopropyl, n-butyl, isobutyl, sec -butyl, and t -butyl.

The term "$C_1-C_4$ alkoxy" represents groups such as methoxy, ethoxy, n-propoxy, isopropoxy, n-butoxy, t-butoxy, and like groups. The term "halogen" refers to the fluoro, chloro, bromo, or iodo groups.

The term "substituted phenyl," as used herein, represents a phenyl group substituted with one or two moieties chosen from the group consisting of halogen, hydroxy, cyano, nitro, $C_1-C_6$ alkyl, $C_1-C_4$ alkoxy, alkoxycarbonyl, carboxymethyl, hydroxymethyl, amino, aminomethyl, and trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 4-cyanophenyl, 4-methylphenyl, 3,4-dimethylphenyl, 4-ethylphenyl, 4-methoxyphenyl, 4-carboxyphenyl, 4-(hydroxymethyl)phenyl, 4-aminophenyl, 4-(methoxycarbonyl) phenyl, 4-trifluoromethylphenyl, and the like.

The term "aryl" represents groups such as phenyl and substituted phenyl as described above. The term "arylalkyl" represents a $C_1-C_4$ alkyl group bearing an aryl group. Representatives of this latter group include benzyl, 1-phenylethyl, 2-phenylethyl, 3-phenylpropyl, 4-phenylbutyl, 2-methyl-2-phenylpropyl, (4-chlorophenyl)methyl, (2,6-dichlorophenyl )methyl, (4-hydroxyphenyl)methyl, (2,4-dinitrophenyl)methyl, and the like.

The term "acyl" represents a hydrogen, $C_1-C_6$ alkyl group, or aryl group attached to a carbonyl group. Typical acyl groups include formyl, acetyl, propionyl, butyryl, valeryl, pivaloyl, caproyl, benzoyl, 4 -nitrobenzoyl, and the like.

The term "alkoxycarbonyl" means a carboxyl group having a $C_1-C_6$ alkyl group attached to the carbonyl carbon through an oxygen atom. Representatives of this group include t-butoxycarbonyl and methoxycarbonyl.

The term "aryloxycarbonyl" represents a carboxyl group bearing an aryl group attached to the carbonyl carbon through an oxygen atom. Representatives of this group include phenoxycarbonyl, (4-chlorophenoxy)carbonyl, and (3-nitrophenoxy)carbonyl.

The term "arylalkoxycarbonyl" represents a carboxyl group having an arylalkyl group attached to the carbonyl carbon through an oxygen atom. Representatives of this group include benzyloxycarbonyl, 2-phenylethoxycarbonyl, 3-phenylpropoxycarbonyl, and the like. The preferred arylalkoxycarbonyl group is benzyloxycarbonyl.

The term "$C_1-C_6$ alkylsulfonyl" means a sulfonyl ($SO_2$) group having a $C_1-C_6$ alkyl group attached to the sulfur atom. Representatives of this group include methanesulfonyl, ethanesulfonyl, n-propanesulfonyl, i-propanesulfonyl, n-butanesulfonyl, and t-butanesulfonyl. Similarly, the term "arylsulfonyl" means a sulfonyl group having an aryl group attached to the sulfur atom. Representatives of this group include benzenesulfonyl, 4-chlorobenzenesulfonyl, 4-(trifluoromethyl)benzenesulfonyl, toluenesulfonyl, and the like.

The term "($C_1-C_6$ alkyl)$_3$silyl" represents a silicon atom having three $C_1-C_6$ alkyl groups, which may be the same or different. Representatives of this group include trimethylsilyl, triethylsilyl, t-butyldimethylsilyl, and the like.

While all the formula IV compounds of the present invention are believed to be useful in synthesis of the formula III compounds, certain compounds of the invention are preferred for such use. Preferably, $R^3$ is acyl, arylsulfonyl, or alkoxycarbonyl, $R^4$ is $CO_2R^5$, $PO(OR^5)_2$,

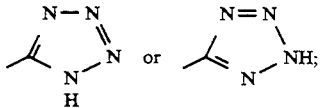

and $R^5$ is hydrogen $C_1-C_6$ alkyl or arylalkyl. More preferably, $R^3$ is acyl or alkoxycarbonyl, $R^4$ is $PO(OR^5)_2$ or $CO_2R^5$, and $R^5$ is $C_1-C_6$ alkyl or arylalkyl. Examples of representative compounds within this more preferred group are 6-(diethyl phosphonomethyl)-2-methoxycarbonyl-decahydroisoquinoline, 6-(diethyl phosphonomethyl)-2acetyldecahydroisquinoline, 6-(dibenzyl phosphonomethyl)-2methoxycarbonyldecahydroisoquinoline, 6-ethoxycarbonylmethyl-2-methoxycarbonyldecahydroisoquinoline, and 6-ethoxycarbonylmethyl-2-acetyldecahydroisoquinoline. Most preferably $R^3$ is alkoxycarbonyl, $R^4$ is $PO(OR^5)_2$, and $R^5$is $C_1-C_6$ alkyl. The most preferred formula IV compound for use in the synthesis of the formula III compound is the compound wherein $R^3$ is methoxycarbonyl, $R^4$ is $PO(OR^5)_2$, and $R^5$ is ethyl.

While all the formula V compounds of the present invention are believed to be useful in the synthesis of the formula III compounds, certain compounds of the invention are preferred for such use. Preferably, $R^3$ is acyl, arylsulfonyl, or alkoxycarbonyl, $R^4$ is $CO_2R^5$, $PO(OR^5)_2$,

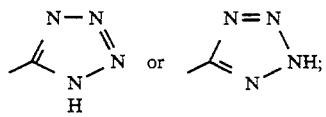

and $R^5$ is hydrogen, $C_1-C_6$ alkyl, or arylalkyl, and $R^6$ is methyl. More preferably, $R^3$ is acyl or alkoxycarbonyl, $R^4$is $PO(OR^5)_2$ or $CO_2R^5$, and $R^5$ is $C_1-C_6$ alkyl or arylalkyl. Examples of representative compounds within this more preferred group are 3-methoxy-2-methoxycarbonyl-6-(diethyl phosphonomethyl)decahydroisoquinoline, 3-methoxy-2 -acetyl-6-(diethyl phosphonomethyl) decahydroisoquinoline, 3-methoxy-2-methoxycarbonyl-6-(dibenzyl phosphonomethyl)-decahydroisoquinoline, 3-methoxy-2-methoxycarbonyl-6-ethoxycarbonylmethyldecahydroisoquinoline, and 3-methoxy-2-acetyl-6-ethoxycarbonylmethyldecahydroisoquinoline. Most preferably $R^3$ is alkoxycarbonyl, $R^4$ is $PO(OR^5)_2$, and $R^5$ is $C_1-C_6$ alkyl. The most preferred formula V compound for use in the synthesis of the formula III compound is the compound wherein $R^3$ is methoxycarbonyl, $R^4$ is $PO(OR^5)_2$, and $R^5$ is ethyl.

While all the formula VI compounds of the present invention are believed to be useful in the synthesis of the formula III compounds, certain compounds of the invention are preferred for such use. Preferably, $R^3$ is acyl, arylsulfonyl, or alkoxycarbonyl, $R^4$ is $CO_2R^5$, $PO(OR^5)_2$,

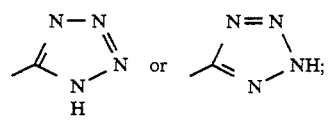

and $R^5$ is hydrogen, $C_1-C_6$ alkyl, or arylalkyl. More preferably, $R^3$ is acyl or alkoxycarbonyl, $R^4$ is $PO(OR^5)_2$ or $CO_2R^5$, and $R^5$ is $C_1-C_6$ alkyl or arylalkyl. Examples of representative compounds within this more preferred group are 3-cyano-6-(diethyl phosphonomethyl)-2-methoxycarbonyldecahydroisoquinoline, 3-cyano-6-(diethyl phosphonomethyl)-2-acetyl-decahydroisoquinoline, 3-cyano-6-(dibenzyl phosphonomethyl)-2-methoxycarbonyldecahydroisoquinoline, 3 -cyano-6-ethoxycarbonylmethyl-2-methoxycarbonyldecahydroisoquinoline, and 3-cyano-6-ethoxycarbonylmethyl-2-acetyldecahydroisoquinoline. Most preferably $R^3$ is alkoxycarbonyl, $R^4$ is $PO(OR^5)_2$, and $R^5$ is $C_1-C_6$ alkyl. The most preferred formula VI compound for use in the synthesis of the formula III compound is the compound wherein $R^3$ is methoxycarbonyl, $R^4$ is $PO(OR^5)_2$, and $R^5$ is ethyl.

The formula IV compounds of the present invention possess three asymmetric carbon atoms. The asymmetric centers are the carbon atom where $R^4CH_2$ is attached to the ring (6), and the two bridgehead carbon atoms (4a and 8a). The configuration for the preferred enantiomer is 4aR,6S,8aR. The relative and absolute stereochemistry of this preferred enantiomer is shown in the following formula.

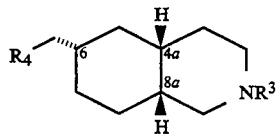

The formula V compounds of the present invention possess four asymmetric carbon atoms. These asymmetric centers are the substituted carbon atom adjacent to the ring $NR^1$ group (3), the carbon atom where $R^4CH_2$ is attached to the ring (6), and the two bridgehead carbon atoms (4a and 8a). Because the formula V compounds are prepared from the formula IV compounds, the stereocenters at C-4a, C-6, and C-8a correspond to the stereochemistry of the formula IV compounds. The present invention includes the compounds wherein the methoxy group at C-3 is in either orientation, α or β. The configurations for the diastereomeric formula V compounds of the present invention are 3S,4aR,6S, 8aR and 3R,4aR,6S,8aR. The relative and absolute stereochemistry of these preferred diastereomers is shown in the following formula.

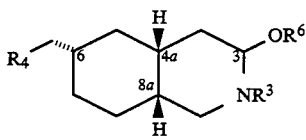

Similarly, the formula VI compounds of the present invention possess four asymmetric carbon atoms. These asymmetric centers are tile substituted carbon atom adjacent to the ring $NR^1$ group (3), the carbon atom where $R^4CH_2$ is attached to the ring (6), and the two bridgehead carbon atoms (4a and 8a). Because the formula VI compounds are prepared from the formula V compounds, the stereocenters of the formula VI correspond to those of the formula V compounds. The configurations for the diastereomeric formula VI compounds are 3S,4aR,6S,8aR and 3R,4aR,6S, 8aR. The relative and absolute stereochemistry of these preferred diastereomers is shown in the following formula.

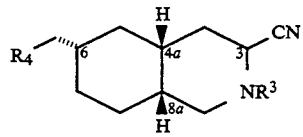

The compounds of the present invention are preferably prepared from a naturally occurring precursor, quinine. This precursor is converted to a substituted piperidine, which possesses the required stereochemistry for the formula III compounds, as outlined in Scheme I.

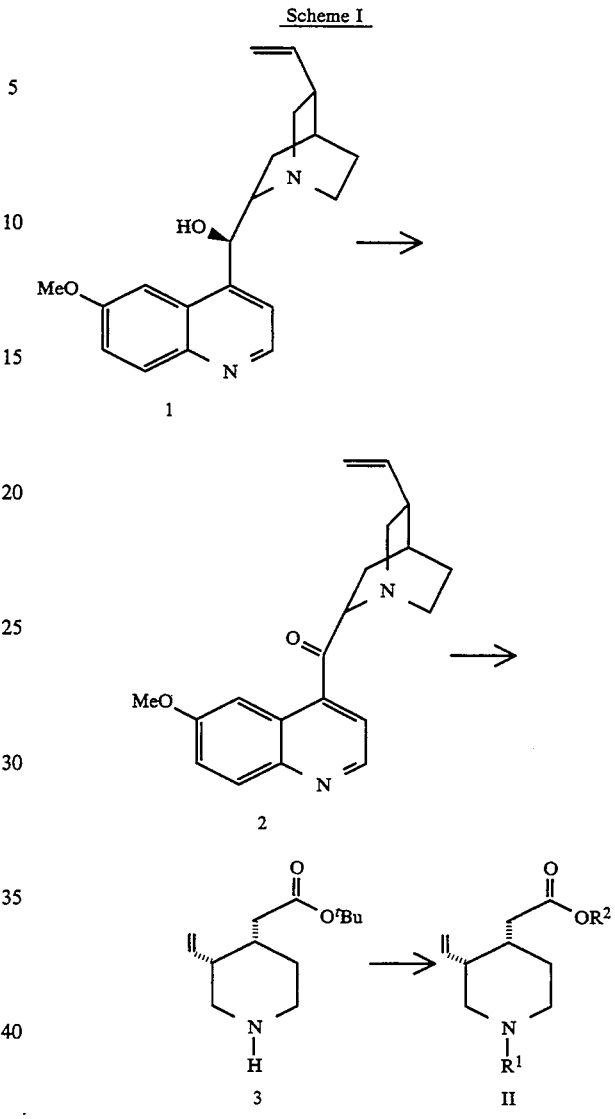

Scheme I

Generally, the naturally occurring alkaloid quinine (1) is oxidized to quininone (2). This compound is then further oxidized, employing a modification to the Uskokovic procedure, to produce meroquinene t-butyl ester (3). Uskokovic et al., Helv. Chim. Acta, 56, 2834–2844 (1973). The ring nitrogen may be protected and the ester group exchanged for another acid-sensitive group to produce, a substituted piperidine intermediate, a formula II compound wherein $R^1$ is hydrogen, $C_1$–$C_6$ alkyl, arylalkyl, acyl, $C_1$–$C_6$ alkylsulfonyl, arylsulfonyl, alkoxycarbonyl, aryloxycarbonyl, or arylalkoxycarbonyl, and $R^2$ is hydrogen, t-butyl, ($C_1$–$C_6$ alkyl)-3silyl, methoxyethoxymethyl, methoxymethyl, tetrahydrofuran-2-yl, tetrahydropyran-2-yl, arylalkyl, cinnamyl, or allyl.

More specifically, quinine (1) is oxidized to quininone (2) by a variety of standard oxidizing agents. Such oxidizing agents include the Jones reagent ($H_2CrO_4$/acetone), the Swern reagent, or other DMSO-based oxidizing agents. Hudlicky, Oxidations in Organic Chemistry, ACS Monograph 186, 21–22 (1990); Mancuso, Huang, and Swern, J. Org. Chem., 43, 2480 (1978); and Epstein & Sweat, Chem. Rev., 67, 247 (1967). The preferred oxidizing agent for this transformation is a combination of benzophenone and potassium t-butoxide as described by Woodward. Woodward, Wendler, and Brutschy, J. Am. Chem. Soc., 67, 1425 (1945). This oxidation is carried out in an organic solvent, such as toluene or benzene, at the reflux temperature of the solvent. When the solvent is toluene, the reaction is typically complete after about 18 hours.

Meroquinene t-butyl ester is prepared by auto-oxidation of quininone (2). This autoxidation is carried out in the presence of potassium t-butoxide in an organic solvent. Suitable organic solvents include alcoholic solvents, such as methanol, ethanol, n-butanol, and t-butanol, or a mixture of an organic solvent, such as tetrahydrofuran, and an alcohol. The preferred solvent for this oxidation is a mixture of tetrahydrofuran and t-butanol (2:1). When an alcohol other than t-butanol is employed as the solvent, the product of the reaction will be the ester corresponding to the alcohol used as a solvent. The reaction is generally carried out at a temperature of about 0° C. to about 30° C., preferably less than 25° C., in the presence of oxygen gas. Preferably, the solution is saturated with oxygen gas by means of a continuous oxygen gas purge.

The meroquinene ester (3) is preferably protected on the ring nitrogen. Methods for the protection of amino groups are generally described in Greene and Wutz, Protective Groups in Organic Synthesis, 309–385 (2d ed., 1991) and McOmie, Protective Groups in Organic Chemistry, 43–74 (1973). The amino group may be protected with a $C_1$–$C_6$ alkyl, arylalkyl, acyl, $C_1$–$C_6$ alkylsulfonyl, arylsulfonyl, alkoxycarbonyl, aryloxycarbonyl, or arylalkoxycarbonyl group. The preferred amino protecting groups are $C_1$–$C_6$ alkyl, arylalkyl, acyl, arylsulfonyl, alkoxycarbonyl, or arylalkoxycarbonyl groups. More preferably, the amino protecting group is a $C_1$–$C_6$ alkyl, acyl, arylsulfonyl, or alkoxycarbonyl group. The most preferred amino protecting groups are the acyl and alkoxycarbonyl group. The methoxycarbonyl group is especially preferred.

The methoxycarbonyl substituted meroquinene t-butyl ester is prepared using standard synthetic organic techniques. Meroquinene t-butyl ester (3) is reacted with methyl chloroformate in the presence of an amine base or an inorganic base. Suitable amine bases for this transformation include N,N-diisopropylethylamine, pyridine, triethylamine, N-methylmorpholine, and the like. Suitable inorganic bases include sodium bicarbonate, sodium carbonate, and potassium carbonate. This reaction preferably is carried out at a temperature of about 0° C. to about 15° C. for a period of about two hours.

The t-butyl ester group may be removed and optionally replaced with another acid-sensitive group. Methods for the hydrolysis of t-butyl esters and subsequent protection of the carboxyl group are generally described in Greene and Wutz, Protective Groups in Organic Synthesis, 224–263 (2d ed., 1991) and McOmie, Protective Groups in Organic Chemistry, 183–210 (1973). The carboxyl group may be protected as the t-butyl, ($C_1$–$C_6$ alkyl)$_3$silyl, methoxyethoxymethyl, methoxymethyl, tetrahydrofuran-2-yl, tetrahydropyran-2-yl, arylalkyl, cinnamyl, or allyl ester. These esters are prepared using standard synthetic organic techniques as described in the above references. The preferred acid-sensitive carboxyl groups are t-butyl, ($C_1$–$C_6$ alkyl)$_3$silyl, methoxyethoxymethyl, methoxymethyl, or tetrahydropyran-2-yl. More preferably, the carboxyl group is a t-butyl, ($C_1$–$C_6$ alkyl)$_3$silyl, or methoxymethyl ester. Most preferably, the acid-sensitive carboxyl group is a t-butyl group.

The formula VII compounds are prepared from the formula II compounds by way of the formula I compounds as outlined in Scheme II.

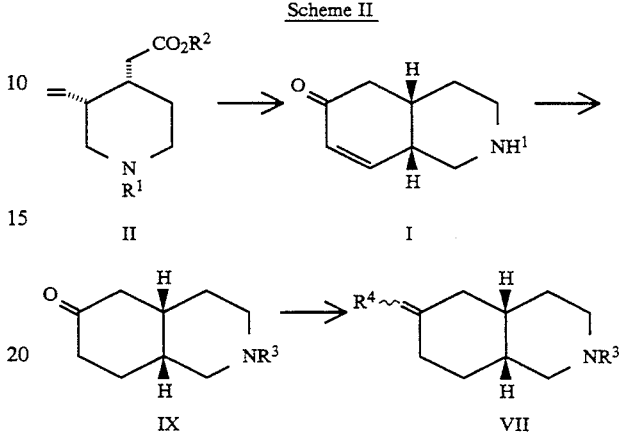

Scheme II

Generally, the formula I compound is produced by sulfuric acid-catalyzed cyclization of the formula II compound. The formula I compound is partially reduced to intermediate IX. This intermediate is then condensed with a Wittig reagent or Horner-Emmons reagent to prepare the formula VII compound.

More specifically, the formula II compound is cyclized to stereospecifically produce a cis-octahydroisoquinol-6-one, formula I compound. The preferred acid catalyst for the cyclization is concentrated sulfuric acid. The reaction may be carried out using sulfuric acid as the solvent, or using a mixture of sulfuric acid and polyphosphoric acid as the solvent. Preferably, the reaction is carried out in concentrated sulfuric acid. The reaction is also carried out at a temperature of about 0° C. to about 20° C. This cyclization is typically complete after a period of about two hours.

The formula I compounds are reduced to prepare the intermediate cis decahydroisoquinol-6-ones, formula IX compounds. The preferred method of reduction is catalytic hydrogenation. Suitable hydrogenation catalysts include palladium on carbon, platinum on carbon, rhodium on carbon, and platinum oxide. The preferred catalyst for this hydrogenation is 10% palladium on carbon. The reaction is typically carried out in an organic solvent, such as ethyl acetate or ethanol. The preferred solvent is ethanol. The reduction is preferably carried out at a hydrogen pressure of about 1 atmosphere and at a temperature of about 20° C. to about 30° C. The reaction is typically complete after about two to about sixteen hours.

The formula IX compound is reacted with a Horner-Emmons reagent or a Wittig reagent to prepare the formula VII compounds. The Horner-Emmons reagent has a general formula ($R^5O$)$_2$POCH$_2$R$^4$, wherein R$^4$ and R$^5$ are as defined previously. The Wittig reagent has the general formula Ph$_3$PCH$_2$R$^4$, wherein R$^4$ is as defined previously. The Horner-Emmons reagent is preferred for use in this reaction. The reaction is generally accomplished by treating the appropriate diethyl phosphonate (Horner-Emmons reagent) or the Wittig reagent with a strong base, such as sodium hydride, to generate the sodium salt of the phosphonate or the ylid. This salt or ylid is then reacted in an organic solvent, such as dry tetrahydrofuran, to provide the formula VII compound. The reaction is typically carried out at the reflux temperature of the solvent. The reaction is generally complete after about 30 minutes to about four hours.

The formula VII compound is stereoselectively reduced to the formula IV compound. A preferred method for this stereoselective reduction is catalytic hydrogenation. Suitable hydrogenation catalysts include palladium on carbon, platinum on carbon, rhodium on carbon, and platinum oxide. Preferably, the reduction is carried out in the presence of 10% palladium on carbon in an inert solvent. Suitable inert solvents include water, ethanol, methanol, and ethyl acetate, preferably ethanol. This stereoselective reduction is typically carried out at a temperature of about 25° C. to about 40° C., and at a hydrogen pressure of about 10 psi to about 50 psi, preferably at about 15 psi. The reaction is typically complete after of a period of about eight to about sixteen hours. The stereoselectivity of this reduction is illustrated by the examples shown in the Table.

TABLE

Stereoselective Reduction of Formula VII Compounds

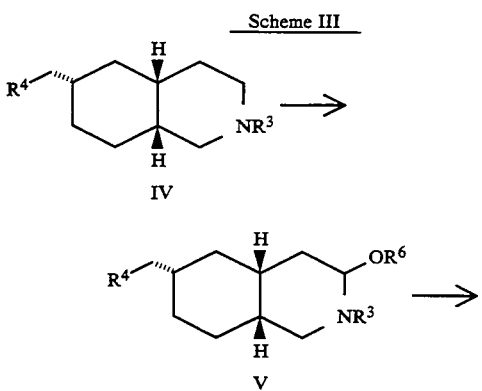

| $R^3$ | $R^4$ | $\alpha:\beta^a$ |
|---|---|---|
| H | $PO_3H_2$ | $15/1^b$ |
| $CO_2Me$ | tetrazole | 3/1 |
| $CO_2Me$ | $CO_2Et$ | 4/1 |
| $CO_2Me$ | $PO_3Et_2$ | 15/1 |

$^a$reactions were carried out in EtOH at ambient temperature with 10% Pd/C and a $H_2$ pressure of 15 psi, yield was >95%.
$^b$reaction carried out in $H_2O$ and a $H_2$ pressure of 50 psi.

The formula III compounds are prepared from the formula IV compounds as outlined in Scheme III.

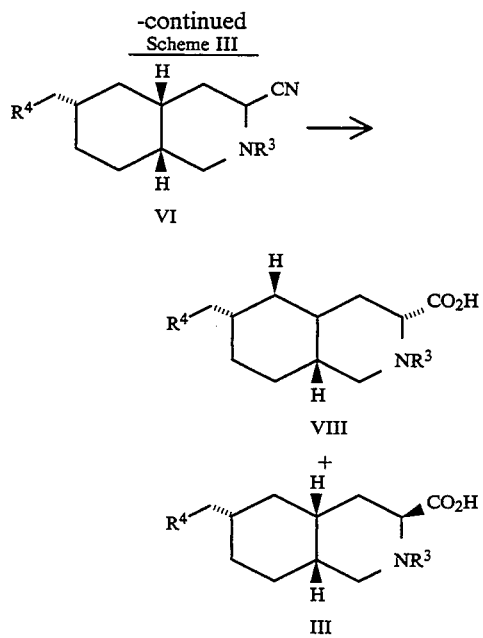

Generally, the formula IV compound is oxidized to the formula V compound. This compound is then cyanated to prepare the formula VI compounds. The formula VI compound is then hydrolyzed to a mixture of C-3 epimers, formula VIII compound and formula III compound. This mixture of C-3 epimers may be treated with a strong base to epimerize the C-3 stereocenter.

More specifically, a formula IV compound is oxidized to the formula V compound. Suitable methods for this oxidation include transition metal catalyzed oxidations in the presence of peroxides and anodic oxidations. The preferred method for this oxidation is anodic oxidation. Generally, a current is applied to carbon plate electrodes immersed into a solution containing the formula IV compound and an electrolyte, such as tetraethylammonium p-toluenesulfonate, in an organic solvent, such as methanol. This anodic oxidation produces a mixture of regioisomers, having a methoxy group at C-1 and C-3, and a mixture of diastereomers, which differ in the C-1 and C-3 stereochemical configuration. This mixture of isomers is preferably used in the subsequent steps without separation.

The formula V compound is cyanated to produce the formula VI compound. Generally, the formula V compound is reacted with trimethylsilyl cyanide in the presence of a Lewis acid in an organic solvent, such as methylene chloride. Suitable Lewis acids include tin(IV) chloride, boron trifluoride etherate, and aluminum chloride; tin(IV) chloride is preferred. Generally, trimethylsilyl cyanide is treated with the Lewis acid at a temperature of about 20° C., then cooled to a temperature of about −60° C. and treated with the solution of the formula V compound in an organic solvent. The cooled solution is then allowed to warm to a temperature of about −30° C., and the reaction is quenched by the addition of aqueous base.

The formula VI compound is hydrolyzed to produce a mixture of the formula III compound and its C-3 epimer, the formula VIII compound, as well as a small amount of the C-1 regioisomer. This hydrolysis is carried out in the presence of an aqueous acid, such as hydrochloric acid or polyphosphoric acid, or a strong organic acid, such as trifluoroacetic acid. The preferred acid for the hydrolysis is concentrated hydrochloric acid. The reaction is typically carried out at a temperature of about 50° C. to about 100° C., preferably at about 80° C. This hydrolysis is typically complete after a period of about 24 to about 30 hours. The diastereomeric products, the formula III compound and the formula VIII compound, may be separated using standard chromatographic techniques, such as high performance liquid chromatography. Preferably, the mixture of epimers and regioisomers is used in the next step.

The mixture of isomers may be treated with a strong base to equilibrate the mixture in favor of the formula III compounds. Suitable strong bases for this equilibration include sodium hydroxide, potassium hydroxide, and a combination of sodium methoxide in methanol. The preferred base for equilibration is 40% potassium hydroxide. When the equilibration is carried out at the reflux temperature of the reaction mixture, the reaction is typically complete after a period of about two and one-half days.

The following examples further illustrate the compounds and the processes of the present invention. The examples are not intended to be limiting to the scope of the invention in any respect, and should not be so construed. Proton nuclear magnetic resonance ($^1$H NMR) spectra were recorded on a GE QE-300 spectrometer at 300.15 MHz. Carbon nuclear magnetic resonance ($^{13}$C NMR) spectra were recorded on a GE QE-300 spectrometer at 75.0 MHz. The reactions were generally monitored for completion using thin layer chromatography (TLC). Thin layer chromatography was generally performed using E. Merck Kieselgel 60 F$_{254}$ plates, 5 cm×10 cm, 0.25 mm silica gel thickness. Silica-gel flash chromatography was performed as described by Still et al. Still, Kahn, and Mitra, *J. Org. Chem.*, 43, 2923 (1978).

PREPARATION 1

Preparation of Quininone

A solution of benzophenone (1.12 kg) in toluene (4 L) was treated with quinine (1.00 kg) and potassium t-butoxide (871 g). The resulting mixture was heated to reflux for six hours, then allowed to cool to room temperature. After about 18 hours, this mixture was cooled to a temperature of about 10° C. to about 15° C. This cold mixture was treated with 2 N hydrochloric acid (4 L) at a rate such that the temperature of the mixture was less than 30° C. The resulting mixture was treated with additional 2 N hydrochloric acid (3 L) and the phases separated. The organic phase was extracted with additional 2 N hydrochloric acid (2×2.5 L). The combined aqueous phase was cooled to a temperature of about 5° C. to about 15° C., and the pH adjusted to pH 9–9.5 with the addition of 5 N sodium hydroxide (ca. 2.6 L). The resulting mixture was stirred at about 5° C. to about 20° C. for one hour. The crystalline material was removed by filtration, rinsed with water (2×1 L), and dried in vacuo at 50° C. to give 1.02 kg of quininone.

PREPARATION 2

Preparation of Meroquinene t-Butyl Ester

A mixture of tetrahydrofuran (200 ml) and t-butanol (100 ml) was added to potassium t-butoxide (43.50 g). The resulting solution was cooled to 4° C. and treated with oxygen gas. This cold solution was treated with a solution of quininone (50 g) in tetrahydrofuran (200 ml) and the rate of oxygen addition was adjusted to maintain the temperature of the solution below 30° C. After the red color had dissipated, the addition of oxygen gas was continued for another five minutes and the temperature of the solution was maintained above 20° C. This mixture was vigorously stirred at 20° C. and treated with acetic acid (40 ml). The resulting slurry was concentrated in vacuo and the residue dissolved in water (20 ml). The pH of the solution was adjusted to pH 9–10 by the addition of concentrated ammonium hydroxide (25 ml). The resulting solution was extracted with ether (4×110 ml). The combined organic extracts were dried over magnesium sulfate, and concentrated in vacuo to give 24.04 g of meroquinene t-butyl ester as a viscous oil.

PREPARATION 3

Preparation of 1-Methoxycarbonylmeroquinene t-Butyl Ester

A solution of meroquinene t-butyl ester (5.15 g) and N,N-diisopropylethylamine (5.98 ml) in methylene chloride (36 ml) was cooled to about 0° C. to about 5° C. This cold solution was treated with methyl chloroformate (2.12 ml) at a rate to maintain the temperature below 15° C. The resulting solution was allowed to warm to room temperature and extracted with 1 N hydrochloric acid. The organic phase was extracted with dilute sodium bicarbonate, dried over sodium sulfate, and concentrated in vacuo to give 5.53 g of the title compound as a brown oil.

$^1$H NMR (CDCl$_3$): δ 5.71–5.83 (m, 1H); 5.06–5.16 (m, 2H); 3.92–4.11 (m, 2H); 3.86 (s, 3H); 3.08 (dd, 1H); 2.92 (m, 1H); 2.37–2.39 (m, 1H); 2.03–2.23 (m, 3H); 1.44 (s, 9H); 1.37–1.57 (m, 2H).

$^{13}$C NMR (CDCl$_3$): δ 171.7, 156.1, 135.1, 117.4, 80.1, 52.4, 48.1, 43.5, 42.1, 38.7, 35.5, 28.0, 27.2.

PREPARATION 4

Preparation of (4aS, 8aS)-2-Methoxycarbonylhexahydro-6-isoquinolone

Concentrated sulfuric acid (19 ml) was cooled to −25° C. and treated with the compound from Preparation 3 (4.71 g). The resulting solution was stirred at 0° C. for 30 minutes and at 20° C. for 1½ hours. This solution was added to ice (64 g), and the resulting mixture extracted with methylene chloride (4×20 ml). The organic extracts were combined and concentrated in vacuo to a residue. The residue was purified by silica-gel flash chromatography, eluting with 20% ethyl acetate/methylene chloride to give 2.95 g of the title compound.

$^1$H NMR (CDCl$_3$): δ 6.79–6.82 (m, 1H); 6.05 (dd, 1H); 3.76–3.94 (m, 2H); 3.70 (s, 3H); 3.36 (dd, 1H); 3.09–3.17 (m, 1H); 2.73 (m, 1H); 2.39–2.56 (m, 3H); 1.56–1.63 (m, 2H).

$^{13}$C NMR (CDCl$_3$): δ 197.8, 155.4, 150.2, 130.4, 52.2, 46.2, 41.9, 41.4, 36.2, 33.2, 26.2.

PREPARATION 5

Preparation of (4aS, 8aR)-2-Methoxycarbonyloctahydro-6-isoquinolone

A mixture of the compound from Preparation 4 (2.29 g) and 10% palladium on carbon (0.23 g) in ethanol (23 ml) was hydrogenated using a hydrogen pressure of 20 psi at ambient temperature. After two hours, the catalyst was removed by filtration and the filtrate concentrated in vacuo to give 2.26 g of the title compound as an oil.

$^1$H NMR (CDCl$_3$): δ 3.92–3.99 (m, 2H); 3.67 (s, 3H); 3.11–3.55 (m, 1H); 2.85–2.95 (m, 1H); 2.53–2.60 (m, 1H); 2.12–2.42 (m, 5H); 1.90–2.03 (m, 2H); 1.46–1.52 (m, 2H).

$^{13}$C NMR (CDCl$_3$): δ 209.6, 155.4, 51.7, 46.6, 45.2, 42.6, 39.0, 36.3, 33.7, 26.1, 24.6.

PREPARATION 6

Preparation of (4aR, 8aR) -6-(Diethyl Phosphonomethylene) -2-Methoxycarbonyldecahydroisoquinoline A mixture of sodium hydride (0.61 g) in tetrahydrofuran (15 ml) was cooled and treated with tetraethyl methylenediphosphonate (6.36 ml). After three hours, the reaction mixture was treated with a solution of the compound from Preparation 5 (2.19 g) in tetrahydrofuran (15 ml). The resulting mixture was heated to reflux. After 2 ½ hours, the reaction solution was added to water (30 ml) and the resulting mixture extracted with ether (2×20 ml). The combined ether extracts were washed with 5 N sodium hydroxide (2×15 ml) and with saturated sodium bicarbonate (15 ml), dried over magnesium sulfate, and concentrated in vacuo to give 4.76 g of the title compound as a oil.

$^1$H NMR (CDCl$_3$): δ 5.29–5.44 (m, 1H); 3.99–4.11 (m, 6H); 3.79–3.98 (m, 2H); 3.66 (s, 3H); 3.14–3.18 (m, 1H); 3.00–3.05 (m, 1H); 2.86 (m, 1H); 1.87–2.48 (m, 5H); 1.29–1.37 (m, 6H); 1.25–1.78 (m, 4H).

$^{13}$C NMR (CDCl$_3$): δ 162.5, 162.4, 155.7, 112.1, 112.0, 109.6, 109.5, 60.8, 60.7, 60.6, 51.9, 47.5, 47.4, 43.1, 42.9, 42.6, 37.1, 36.8, 36.0, 35.8, 35.3, 35.3, 35.2, 34.8, 34.7, 29.9, 29.8, 25.9, 25.6, 25.5, 25.4, 25.3, 15.8.

EXAMPLE 1

Preparation of (4aR, 6S, 8aR) -6- (Diethyl Phosphonomethyl) -2-Methoxycarbonyldecahydroisoquinoline A mixture of the compound from Preparation 6 (4.76 g) and 10% palladium on carbon (0.6 g) in ethanol (30 ml) was hydrogenated at 40° C. and a hydrogen pressure of 15 psi. After sixteen hours, the reaction mixture was added to methylene chloride (200 ml). This mixture was filtered through silica-gel, and the silica-gel washed with 20% ethanol/methylene chloride (250 ml). The filtrates were combined and concentrated in vacuo to a residue. The residue is purified by silica-gel flash chromatography, eluting with ethyl acetate, to give 4.52 g of the title compound.

$^1$H NMR (CDCl$_3$): δ 4.03–4.14 (m, 6H); 3.70–4.00 (m, 2H); 3.67 (s, 3H); 2.79–2.98 (m, 2H); 1.29–1.91 (m, 8H); 1.01–1.13 (m, 1H).

$^{13}$C NMR (CDCl$_3$): δ 155.4, 60.7, 60.6, 51.7, 42.5, 38.5, 33.5, 33.0, 32.4, 32.3, 32.2, 32.0, 31.7, 30.4, 28.5, 28.3, 15.9, 15.8.

EXAMPLE 2

Preparation of (3SR, 4aR, 6S, 8aR)-6-(Diethyl Phosphonomethyl)-3-Methoxy-2-Methoxycarbonyldecahydroisoquinoline Four carbon plate electrodes were immersed into a solution containing the compound from Example 1 (250 mg), tetraethylammonium p-toluenesulfonate (21 mg), in methanol (10 ml). A constant current of 0.5 A was applied to the electrodes. Additional methanol (7.8 ml) was added to the reaction to replace methanol which was lost due to evaporation. After 550 coulombs of current had passed, the electrodes were removed and the solution was added to 10% brine. This mixture was extracted with ether (3×15 ml). The combined ether extracts were washed with water and with brine, dried over magnesium sulfate, and concentrated in vacuo at room temperature to give 237 ml of the title compound as an oil. The material was stored in the refrigerator and used in the next step without further purification.

EXAMPLE 3

Preparation of (3SR, 4aR, 6S, 8aR)-3-Cyano-6-(Diethyl Phosphonomethyl)-2-methoxycarbonyldecahydroisoquinoline A solution of trimethylsilyl cyanide (10 ml) in methylene chloride (72 ml) was cooled to 20° C. and treated with tin(IV) chloride (8.8 ml) at a rate such that the temperature of the solution was less than 30° C. After the addition of the tin(IV) chloride was complete, the solution was cooled to −60° C. and treated with a solution of the compound prepared as described in Example 2 (14.36 g) in methylene chloride (72 ml). After 20 minutes at −60° C., the solution was warmed to −30° C. over 10 minutes. This mixture was added to water and the phases separated. The aqueous phase was extracted with methylene chloride (50 ml). The organic phases were combined and treated with 50% caustic and with ethyl acetate. The organic phase was removed and the aqueous phase was extracted with ethyl acetate. The combined organic phases were washed with water and with brine, and concentrated in vacuo to give 13.17 g of the title compound as an oil.

EXAMPLE 4

Preparation of (3SR, 4aR, 6S, 8aR)-6-Phosphonomethyldecahydroisoquinoline-3-Carboxylic Acid A mixture of the compound from Example 3 (12.64 g) and concentrated hydrochloric acid (40 ml) was heated to reflux. After 26 ½ hours, the mixture was allowed to cool to 80° C. and treated with charcoal (2 g). This mixture was heated to reflux for 10 minutes, then the charcoal was removed by filtration. The solids were washed with water (60 ml). The filtrate and wash were combined and extracted with methylene chloride (2×20 ml) and with chloroform (1×20 ml), and concentrated in vacuo to a brown foam containing about 60% of the title compound.

EXAMPLE 5

Preparation of (3S, 4aR,6S, 8aR)-6-Phosphonomethyldecahydroisoquinoline-3-Carboxylic Acid The mixture from Example 4 (9.15 g) was added to 40% potassium hydroxide (45 ml). The resulting solution was heated to reflux. After 2½ days, the reaction mixture was allowed to cool to room temperature, neutralized with hydrochloric acid, and concentrated in vacuo to a brown oil. High performance liquid chromatographic (HPLC) analysis (WATERS NOVA C18 columnm, 8 mm×100 mm, elution with 0.1%H$_3$PO$_4$, 1%MeOH/H$_2$O) of the residue shows a mixture comprising 58.8% of the title compound.

[α]$_{589}$=−36.8° (c=5.0, H$_2$O).

Mass spectrum: m/z=278 (M+I).

IR (KBr): 1100, 1740, 2920, 3410 cm$^{-1}$.

$^1$H NMR (dioxane-d$_8$): δ 3.46 (dd, 1H), 3.03 (t,1H), 2.85 (dd, 1H), 1.25–2.03 (m,12H), 0.88–1.01 (m, 1H).

$^{13}$H NMR (dioxane-d$_8$): δ 176.2, 55.1, 43.2, 37.5, 34.5, 33.5, 33.4, 31.4, 29.1, 28.5.

Analysis calculated for C$_{11}$H$_{20}$NO$_5$P·½H$_2$): C, 46.15; H, 7.39; N, 4.89. Found: C, 46.12; H, 6.99; N, 5.08.

We claim:

1. A compound of the formula

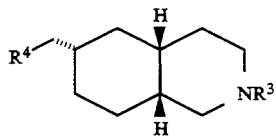

IV wherein

R$^3$ is hydrogen, C$_1$–C$_6$ alkyl, arylalkyl, acyl, C$_1$–C$_6$ alkylsulfonyl, arylsulfonyl, alkoxycarbonyl, aryloxycarbonyl, or arylalkoxycarbonyl;

R$^4$ is CO$_2$R$^5$, CON(R$^5$)$_2$, PO(OR$^5$)$_2$,

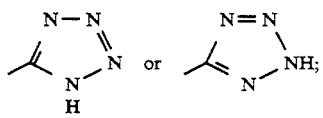

R$^5$ is hydrogen, C$_1$–C$_6$ alkyl, or arylalkyl.

2. The compound of claim 1 wherein R$^3$ is hydrogen or alkoxycarbonyl.

3. The compound of claim 2 wherein R$^4$ is PO(OR$^5$)$_2$.

4. The compound of claim 5 wherein R$^5$ is hydrogen or C$_1$–C$_6$ alkyl.

5. The compound of claim 4 wherein R$^3$ is methoxycarbonyl and R$^5$ is ethyl.

6. A compound of the formula

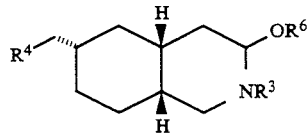

V wherein

R$^3$ is hydrogen, C$_1$–C$_6$ alkyl, arylalkyl, acyl, C$_1$–C$_6$ alkylsulfonyl, arylsulfonyl, alkoxycarbonyl, aryloxycarbonyl, or arylalkoxycarbonyl;

R$^4$ is CO$_2$R$^5$, CON(R$^5$)$_2$, PO(OR$^5$)$_2$,

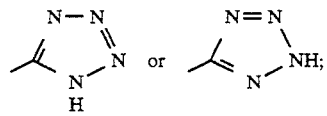

R$^5$ is hydrogen, C$_1$–C$_6$ alkyl, or arylalkyl; and R$^6$ is hydrogen, C$_1$–C$_4$ alkyl, —OH, —O—(C$_1$–C$_4$ alkyl), or —O—aryl.

7. The compound of claim 6 wherein R$^3$ is hydrogen or alkoxycarbonyl and R$^6$ is methyl.

8. The compound of claim 7 wherein R$^4$ is PO(OR$^5$)$_2$.

9. The compound of claim 8 wherein R$^5$ is hydrogen or C$_1$–C$_6$ alkyl.

10. The compound of claim 9 wherein R$^3$ is methoxycarbonyl and R$^5$ is ethyl.

11. A compound of the formula

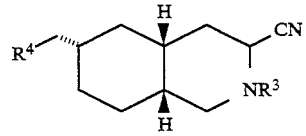

VI wherein

R$^3$ is hydrogen, C$_1$–C$_6$ alkyl, arylalkyl, acyl, C$_1$–C$_6$ alkylsulfonyl, arylsulfonyl, alkoxycarbonyl, aryloxycarbonyl, or arylalkoxycarbonyl;

R$^4$ is CO$_2$R$^5$, CON(R$^5$)$_2$, PO(OR$^5$)$_2$.

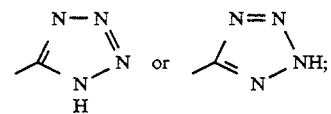

R$^5$ is hydrogen, C$_1$–C$_6$ alkyl, or arylalkyl.

12. The compound of claim 11 wherein R$^3$ is hydrogen or alkoxycarbonyl.

13. The compound of claim 12 wherein R$^4$ is PO(OR$^5$)$_2$.

14. The compound of claim 13 wherein R$^5$ is hydrogen or C$_1$–C$_6$ alkyl.

15. The compound of claim 14 wherein R$^3$ is methoxycarbonyl and R$^5$ is ethyl.

* * * * *

UNITED STATES PATENT AND TRADEMARK OFFICE
CERTIFICATE OF CORRECTION

PATENT NO. : 5,338,851
DATED : August 16, 1994
INVENTOR(S) : Bret E. Huff, Vien V. Khau, Michael J. Martinelli, and Barry C. Peterson It is certified that error appears in the above-indentified patent and that said Letters Patent is hereby corrected as shown below:

Column 12, line 11, the structure reads:

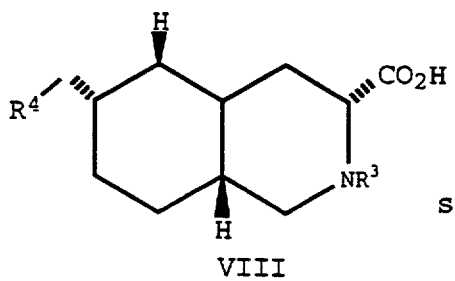   should be   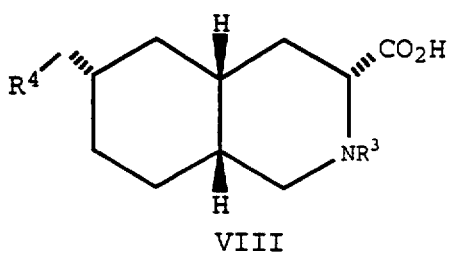

Column 17, line 30, "claim 5" should read --claim 3--.

Column 18, line 8, "$R^6$is" should read --$R^6$ is--.

Signed and Sealed this

Fourteenth Day of March, 1995

Attest:

BRUCE LEHMAN

Attesting Officer   Commissioner of Patents and Trademarks